United States Patent [19]

Raddatz et al.

[11] Patent Number: 5,532,255
[45] Date of Patent: * Jul. 2, 1996

[54] ADHESION RECEPTOR ANTAGONISTS

[75] Inventors: Peter Raddatz, Seeheim-Jugenheim; Joachim Gante, Darmstadt; Horst Juraczyk, Seeheim; Hanns Wurziger, Darmstadt; Helmut Prücher, Heppenheim; Sabine Bernotat-Danielowski, Bad Naumheim; Guido Melzer, Hofheim/Ts., all of Germany

[73] Assignee: Merck Patent Gesellschaft mit beschrankter Haftung, Darmstadt, Germany

[*] Notice: The portion of the term of this patent subsequent to Jul. 21, 2014, has been disclaimed.

[21] Appl. No.: 234,691

[22] Filed: Apr. 29, 1994

[30] Foreign Application Priority Data

May 1, 1993 [DE] Germany ............... 43 14 378.4
Feb. 22, 1994 [DE] Germany ............... 44 05 633.8

[51] Int. Cl.$^6$ .............. A61K 31/42; A61K 31/445; C07D 413/06
[52] U.S. Cl. .............. 514/326; 514/210; 514/212; 514/255; 514/278; 514/376; 540/200; 540/362; 540/603; 544/369; 546/18; 546/229; 548/229; 548/962
[58] Field of Search .............. 540/603, 200, 540/362; 546/209, 18; 548/229, 962; 544/369; 514/210, 212, 255, 278, 326, 376

[56] References Cited

U.S. PATENT DOCUMENTS

| | | | |
|---|---|---|---|
| 3,687,965 | 8/1972 | Fauran et al. | 260/307 C |
| 4,886,794 | 12/1989 | Walsh | 514/211 |
| 4,970,217 | 11/1990 | Prücher et al. | 514/327 |
| 5,084,466 | 1/1992 | Alig et al. | 514/353 |
| 5,086,055 | 2/1992 | Walsh | 514/252 |
| 5,232,931 | 8/1993 | Prücher et al. | 514/321 |

FOREIGN PATENT DOCUMENTS

| | | |
|---|---|---|
| 0381033 | 8/1990 | European Pat. Off. . |
| 0459256 | 12/1991 | European Pat. Off. . |
| 0462960 | 12/1991 | European Pat. Off. . |

OTHER PUBLICATIONS

Ruoslahti et al "New Perspective in Cell Adhesion: RGD and Integrins" Science 238 491–496 (1987).
Bajnsz et al "High Active and Selective Anticoagulants" J. Med. Chem. 33 pp. 1729–1735 (1990).
Hartman et al "Non-Peptide Fibrinogen Receptor Antagonists" J. Med. Chem. 35 4640–4642 (1992).
Born. Nature, 194(4832):927–929 (Jun. 9, 1962).

*Primary Examiner*—Ceila Chang
*Attorney, Agent, or Firm*—Millen, White, Zelano & Branigan

[57] ABSTRACT

Compounds of the formula

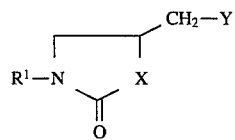

in which $R^1$, X and Y have the meanings defined herein, and their salts, inhibit the binding of fibrinogen to the fibrinogen receptor and can be used for treating thrombosis, stroke, cardiac infarction, inflammations, arteriosclerosis, osteoporosis and tumors.

22 Claims, No Drawings

ADHESION RECEPTOR ANTAGONISTS

The invention relates to novel compounds of the formula I:

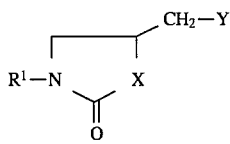

in which

X is O, S, NH or NA,

Y is an aziridino, azetidino, pyrrolidino, piperidino, 1-oxa-8-azaspiro[4.5]dec-8-yl, hexahydroazepino or 4-$R^4$-piperazino radical which is unsubstituted or substituted once by $R^2$ and optionally additionally substituted by an OZ, SZ or N(Z)$_2$ group and/or by carbonyl oxygen, Z is in each case H, A, phenyl-$C_kH_{2k}$ or Ac, $R^1$ is a phenyl radical which is substituted once by CN, $H_2N$—$CH_2$—, (A)$_2$N—$CH_2$—, $H_2N$—C(=NH)—, $H_2N$—C(=NH)—NH—, $H_2N$—C(=NH)—NH—$CH_2$—, HO—NH—C(=NH)— or HO—NH—C(=NH)—NH—, $R^2$ is —$C_mH_{2m}$—COOR$^3$ or —$C_nH_{2n}$—O—$C_pH_{2p}$—COOR$^3$, $R^3$ is H, A or benzyl, $R^4$ is H, A, benzyl or —$C_mH_{2m}$—COOR$^3$, A is in each case alkyl having 1–6 C atoms, Ac is acyl having 1–11 C atoms, k and m are in each case 0, 1, 2 or 3, n is 0, 2 or 2, and p is 1, 2 or 3, and salts thereof.

An object of the invention is to provide novel compounds with valuable properties, especially those which can be used for the preparation of drugs.

Similar compounds are known from EP-A1-0 381 003.

Upon further study of the specification and appended claims, further objects and advantages of this invention will become apparent to those skilled in the art.

These objects have been achieved by the compounds according to the invention. It has been found that the compounds of formula I and their solvates and salts possess valuable pharmacological properties coupled with a good tolerance. In particular, they inhibit the binding of fibrinogen, fibrinonectin and the von Willebrand factor to the fibrinogen receptor of blood platelets (glycoprotein IIb/IIIa), as well as the binding of these proteins, and further adhesive proteins, such as vitronectin, collagen and laminin, to the corresponding receptors on the surface of various cell types. The compounds consequently influence cell-cell and cell-matrix interactions. They prevent the development of blood-platelet thrombi in particular, and can therefore be used for the treatment of thrombosis, stroke, cardiac infarction, inflammations and arteriosclerosis. In addition, the compounds have an effect on tumor cells, by preventing them from forming metastases. Consequently, they can also be employed as anti-tumor agents.

There is evidence that tumor cells spreading from a solid tumor into the vasculature are carried by microthrombi and thus are protected from being detected by cells of the immune system. The second step of attachment to the vessel wall seems to be facilitated by microthrombi as well. Since the formation of thrombi is mediated by fibrinogen binding to the fibrinogen receptor (glycoprotein IIb/IIIa) on activated platelets, fibrinogen-binding inhibitors are expected to be effective as antimetastatics.

Also, since fibrinogen-binding inhibitors are ligands with fibrinogen receptor on platelets, they can be used as diagnostic tools for detection and localization of thrombi in the vascular in vivo. Thus, for example, in accordance with known procedures, the fibrinogen-binding inhibitors can be labeled with a signal generating or detectable moiety whereby, once the labeled fibrinogen-binding inhibitor is bound to a fibrinogen receptor on platelets, it is possible to detect and locate thrombi.

Fibrinogen-binding inhibitors are also very effective as research tools for studying the metabolism of platelets in the different activation states or intracellular signalling mechanisms of the fibrinogen receptor. For example, as described above, fibrinogen-binding inhibitor can be labeled with a signal generating or detectable moiety. The fibrinogen-binding inhibitor-signal generating/detectable moiety conjugate can then be employed in vitro as a research tool. By binding the conjugate to fibrinogen receptors, it is possible to monitor and study the metabolism of platelets, as well as the activation states and signalling mechanisms of the fibrinogen receptors.

The compounds are also suitable as anti-microbial active substances which are able to prevent infections, for example, those initiated by bacteria, fungi or yeasts. The substances can therefore preferably be given as accompanying anti-microbial active substances, when organisms are subjected to interventions in which exogenous, for example, biomaterials, implants, catheters, or pacemakers, are employed. They act as antiseptics. Antimicrobial activity of the compounds can be demonstrated by the procedure described by P. Valentin-Weigand et al., Infection and Immunity, 2851–2855 (1988).

The properties of the compounds can be demonstrated by methods which are described in EP-A1-0 462 960. The inhibition of the binding of fibrinogen to the fibrinogen receptor can be demonstrated by the method given in EP-A1-0 381 033. The inhibitory effect on blood platelet aggregation can be demonstrated in vitro by the method of Born (Nature, 4832, 927–929, 1962).

The invention relates additionally to a process for preparing a compound of the given formula I, and its salts, characterized in that (a) a compound of the formula I is liberated from one of its functional derivatives by treating with a solvolyzing or hydrogenolyzing agent, or in that (b) a compound of the formula II

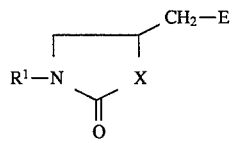

in which

E is Cl, Br, I, or a reactive esterified OH group, and $R^1$ and X have the abovementioned meanings, is reacted with an amino compound of the formula III

H—Y        III in which

Y has the abovementioned meaning, or in that (c) a compound of the formula IV $R^1$—NH—CH$_2$—CH(XH)—CH$_2$—Y     IV in which R$^1$, X and Y have the abovementioned meanings, or one of its reactive derivatives, is reacted with a reactive derivative of carbonic acid, or in that (d) in order to prepare a guanidino compound of the formula I (R$^1$=phenyl radical substituted once by H$_2$N—C(=NH)—NH—), an amino compound corresponding to the formula I, which, however, contains an aminophenyl group in place of the radical R$^1$, is treated with an amidinating agent, and/or in that, in a compound of the formula I, one or both radicals R$^1$ and/or Y is/are transformed into (an) other radical(s) R$^1$ and/or Y, and/or a compound of the formula I is converted into one of its salts by treatment with an acid or a base.

The compounds of the formula I possess at least one chiral center and can therefore occur in several enantiomeric forms. All these forms (e.g., D and L forms), and their mixtures (e.g., the DL forms), are included in the formula I.

Both in the above and in the following, the radicals or parameters X, Y, Z, R$^1$ to R$^4$, A, Ac, k, m, n, p and E have the meanings given in the formulae I or II, unless otherwise expressly indicated. In the case where several groups A and/or Z are present in the molecule I, II and/or III, they can be identical or different from one another.

In the above formulae, the group A has 1–6, preferably 1,2, 3 or 4, C atoms. Specifically, A preferably is methyl, ethyl, propyl, isopropyl, butyl, isobutyl, sec-butyl or tert-butyl, and, additionally, also pentyl, 1-, 2- or 3-methylbutyl, 1,1-, 1,2- or 2,2-dimethylpropyl, 1-ethylpropyl, hexyl or 1-, 2-, 3- or 4-methylpentyl.

X is preferably O, or else S, NH or NA, e.g., N—CH$_3$.

Y is preferably 3-(R$^3$OOC)-azetidino, 3-(R$^3$OOC—CH$_2$—O—)-azetidino, 2-(R$^3$OOC—)-pyrrolidino, 3-(R$^3$OOC—)-pyrrolidino, 2-(R$^3$OOC—)-piperidino, 3-(R$^3$OOC—)-piperidino, 4-(R$^3$OOC—)-piperidino, 2-(R$^3$OOC—CH$_2$—)-piperidino, 3-(R$^3$OOC—CH$_2$—)-piperidino, 4-(R$^3$OOC—CH$_2$—)-piperidino, 4-(R$^3$OOC—CH$_2$CH$_2$—)-piperidino, 4-hydroxy-4-(R$^3$OOC)-piperidino, 4-hydroxy-4-(R$^3$OOC—CH$_2$—)-piperidino, 4-amino-4-(R$^3$OOC)-piperidino, 4-amino-4-(R$^3$OOC—CH$_2$—)piperidino, 3-oxo-4-(R$^3$OOC—CH$_2$—)-piperidino, 2-(R$^3$OOC—CH$_2$—O—)-piperidino, 3-(R$^3$OOC—CH$_2$—O—)-piperidino, 4-(R$^3$OOC—CH$_2$—O—)-piperidino, 1-oxa-2-oxo-8-azaspiro[4.5]dec-8-yl, 2-, 3- or 4-(R$^3$OOC)-hexahydroazepino, 4-(R$^3$OOC—CH$_2$—)-piperazino, 4-(R$^3$OOC—CH$_2$CH$_2$—)-piperazino, 2-(R$^3$OOC)-piperazino, 3-(R$^3$OOC)-piperazino, or 4-benzyl-3-(R$^3$OOC)-piperazino.

Z is preferably H, more preferably A such as methyl or ethyl, phenyl, benzyl, acetyl or benzoyl.

R$^1$ is preferably a phenyl radical, which is substituted, as indicated, in the 4 position, or else in the 2 or 3 position, those which are specifically preferred being 2-, 3- or (in particular) 4-cyanophenyl, 2-, 3- or (in particular) 4-aminomethylphenyl, 2-, 3- or (in particular) 4-dimethylaminomethylphenyl, 2-, 3- or (in particular) 4-amidinophenyl, 2-, 3- or 4-guanidinophenyl or 2-, 3- or 4-guanidinomethylphenyl, 2-, 3- or (in particular) 4-hydroxyamidinophenyl.

R$^2$ is preferably —COOR$^3$, —CH$_2$COOR$^3$ or —O—CH$_2$COOR$^3$.

R$^3$ is preferably H, methyl, ethyl, tert-butyl or benzyl.

R$^4$ is preferably H, methyl, ethyl, benzyl or —CH$_2$COOR$^3$.

Ac is preferably alkanoyl having 1–6 carbon atoms, such as formyl, acetyl, propionyl, butyryl, isobutyryl, valeryl or caproyl, and also benzoyl, tolyl, 1- or 2-naphthoyl or phenylacetyl.

The parameters k and m are preferably 0 or 1. The parameter n is preferably 0. The parameter p is preferably 1.

Those compounds of the formula I are preferred in which at least one of the indicated radicals, groups and/or parameters has one of the indicated preferred meanings. Some groups of preferred compounds are those of the formulae Ia to Id which correspond to the formula I where, however, in Ia X is O;

in Ib X is O, and

R$^1$ is cyanophenyl;

in Ic X is O, and

R$^1$ is aminomethylphenyl;

in Id X is O, and

R$^1$ is amidinophenyl.

Furthermore, compounds are preferred which are of the formulae Ie, as well as Iae, Ibe, Ice and Ide, which correspond to the formulae I, Ia, Ib, Ic and Id where, however in addition, Y is 3-R$^2$-azetidino, 2-R$^2$-pyrrolidino, 2-R$^2$-piperidino, 3-R$^2$-piperidino, 4-R$^2$-piperidino, 4-R$^2$-piperazino or 3-R$^2$-4-R$^4$-piperazino, R$^2$ is —COOR$^3$, —CH$_2$COOR$^3$ or —OCH$_2$COOR$^3$, and R$^4$ is —CH$_2$COOR$^3$.

Smaller, selected, groups of compounds are those of the formulae If and Ig. They correspond to the formula I where, however, in If X is O, Y is 3-(R$^3$OOC—CH$_2$—O—)-azetidino, 2-(R$^3$OOC—)-pyrrolidino, 2-, 3- or 4-(R$^3$OOC—)-piperidino, 4-(R$^3$OOC—CH$_2$—)-piperidino, 3- or 4-(R$^3$OOC—CH$_2$—O—)-piperidino, 4-(R$^3$OOC—CH$_2$)-piperazino or 3-(R$^3$OOC—)-4-R$^4$-piperazino, R$^1$ is 4-cyanophenyl, 4-aminomethylphenyl, 4-amidinophenyl, or 4-guanidinomethylphenyl, R$^3$ is H, C$_1$–C$_4$-alkyl or benzyl and R$^4$ is H or benzyl, and in Ig X is O, Y is 4-(R$^3$OOC—)-piperidino or 4-(R$^3$OOC—CH$_2$O—)-piperidino, R$^1$ is 4-cyanophenyl, 4-aminomethylphenyl or 4-amidinophenyl, and R$^3$ is H, C$_1$–C$_4$-alkyl or benzyl.

The compounds of the formula I, and also the starting compounds for their preparation, are otherwise prepared by methods which are known per se, as described in the literature (e.g., in the standard works, such as Houben-Weyl, Methoden der organischen Chemie (Methods of Organic Chemistry), Georg-Thieme Verlag, Stuttgart; additionally EP-A1-0381033 and EP-A1-0462960), specifically under reaction conditions which are known, and suitable, for the reactions. In this context, use can also be made of variants which are known per se but which are not mentioned here in detail.

If desired, the starting compounds can also be formed in situ, such that they are not isolated from the reaction mixture but, instead, immediately further reacted to give the compounds of the formula I.

The compounds of the formula I can be obtained by liberating them from their functional derivatives by solvolysis, in particular hydrolysis, or by hydrogenolysis.

Preferred starting compounds for the solvolysis or hydrogenolysis are those which, while otherwise corresponding to the formula I, contain corresponding protected amino and/or hydroxyl groups in place of one or more free amino and/or hydroxyl groups, preferably those which carry an amino protective group in place of an H atom which is linked to an N atom, in particular those which carry an R'—N— group, where R' is an amino protective group, in place of an HN group, and/or those which carry a hydroxyl protective group in place of the H atom of a hydroxyl group, e.g., those which correspond to the formula I but carry a —COOR" group, where R" is a hydroxyl protective group, in place of a —COOH group.

Several—identical or different—protected amino and/or hydroxyl groups may also be present in the molecule of the starting compouund. If the protective groups which are present differ from each other, they can in many cases be eliminated selectively.

The expression "amino protective group" is well known and relates to groups which are suitable for protecting (for blocking) an amino group from chemical reactions but which are readily removable once the desired chemical reaction at another site in the molecule has been carried out. Typical groups of this nature are, in particular, unsubstituted or substituted acyl, aryl (e.g., 2,4-dinitrophenyl (DNP)), aralkoxymethyl (e.g., benzyloxymethyl (BOM)) or aralkyl (e.g., benzyl, 4-nitrobenzyl or triphenylmethyl) groups. Since the amino protective groups are removed following the desired reaction (or sequence of reactions), their nature and size is otherwise not critical; however, those are preferred which have 1–20, in particular 1–8, C atoms. In connection with the present process, the expression "acyl group" is to be interpreted in the widest sense. It embraces acyl groups derived from aliphatic, araliphatic, aromatic or heterocyclic carboxylic acids or sulfonic acids, such as, in particular, alkoxycarbonyl, aryloxycarbonyl and, above all, aralkoxycarbonyl groups. Examples of acyl groups of this nature are alkanoyl, such as acetyl, propionyl or butyryl; aralkanoyl, such as phenylacetyl; aroyl, such as benzoyl or tolyl; aryloxyalkanoyl, such as phenoxyacetyl; alkoxycarbonyl, such as methoxycarbonyl, ethoxycarbonyl, 2,2,2,-trichloroethoxycarbonyl, isopropoxycarbonyl, tert-butoxycarbonyl (BOC) or 2-iodoethoxycarbonyl; aralkyloxycarbonyl, such as benzyloxycarbonyl (CBZ), 4-methoxybenzyloxycarbonyl or 9-fluorenylmethoxycarbonyl (FMOC). Those amino protective groups which are preferred are BOC, DNP and BOM, and, additionally, CBZ, benzyl and acetyl.

The expression "hydroxyl protective group" is likewise well known and relates to groups which are suitable for protecting a hydroxyl group from chemical reactions but which are readily removable once the desired chemical reaction has been carried out at another site in the molecule. Typical groups of this nature are the abovementioned unsubstituted or substituted aryl, aralkyl or acyl groups, and additionally, alkyl groups. The nature and size of the hydroxyl protective groups is not critical, since they are removed once more following the desired chemical reaction or sequence of reactions; groups having 1–20, in particular 1–10, C atoms are preferred. Examples of hydroxyl protective groups are, inter alia, tert-butyl, benzyl, p-nitrobenzoyl, p-toluenesulfonyl and acetyl, with benzyl and acetyl being particularly preferred.

The functional derivatives of the compounds of the formula I to be used as starting compounds can be prepared by customary methods, such as are described, for example, in said standard works and patent applications, e.g., by the reaction of compounds which correspond to the formulae II and III, with, however, at least one of these compounds containing a protective group in place of a H atom.

The liberation of the compounds of the formula I from their functional derivatives is achieved—in dependence on the protective group used—e.g., using strong acids, expediently using trifluoroacetic acid or perchloric acid, or else using other strong inorganic acids, such as hydrochloric acid or sulfuric acid, strong organic carboxylic acids, such as trichloroacetic acid, or sulfonic acids, such as benzenesulfonic acid or p-toluenesulfonic acid. It is possible, but not always necessary, for an additional inert solvent to be present.

Suitable inert solvents are, preferably, organic, for example carboxylic, acids, such as acetic acid, ethers, such as tetrahydrofuran or dioxane, amides, such as dimethylformamide (DMF), halogenated hydrocarbons, such as dichloromethane, sulfoxides such as dimethyl sulfoxide (DMSO), and, in addition, alcohols, such as methanol, ethanol or isopropanol, as well as water. Additionally mixtures of the abovementioned solvents are suitable. Trifluoroacetic acid is preferably used in excess without addition of any further solvent; perchloric acid is used in the form of a mixture consisting of acetic acid and 70% perchloric acid in the ratio 9:1. The reaction temperatures for the cleavage are expediently about 0°–50°; preferably 15°–30° (room temperature).

The BOC group can, for example, preferably be eliminated using 40% trifluoroacetic acid in dichloromethane, or using about 3 to 5N HCl in dioxane, at preferably about 15°–60°, and the FMOC group using an approximately 5–20% solution of dimethylamine, diethylamine or piperidine in DMF at preferably about 15°–50°. Elimination of the DNP group is also achieved, for example, using an approximately 3–10% solution of 2-mercaptoethanol in DMF/water at preferably about 15°–30°.

Protective groups (e.g., BOM, CBZ or benzyl) which are removable by hydrogenolysis can be eliminated, for example, by treating with hydrogen in the presence of a catalyst (e.g., a precious metal catalyst such as palladium, expediently on a carrier such as carbon). In this context, suitable solvents are those given above, in particular, for example, alcohols, such as methanol or ethanol or amides, such as DMF. The hydrogenolysis is carried out, as a rule, at temperatures of preferably about 0°–100° and pressures of preferably about 1–200 bar, especially at 20°–30° and 1–10 bar. Hydrogenolysis of the CBZ group is achieved satisfactorily, for example, on 5–10% Pd-C in methanol at preferably about 20°–30°.

Compounds of the formula I can preferably also be obtained by reacting a compound of the formula II with a base of the formula III. The known methods of N-alkylation are then expediently utilized.

The leaving group E is preferably Cl, Br, I, $C_1$–$C_6$-alkylsulfonyloxy, such as methanesulfonyloxy or ethanesulfonyloxy, or $C_6$–$C_{10}$-arylsulfonyloxy, such as benzenesulfonyloxy, p-toluenesulfonyloxy or 1- or 2-naphthalenesulfonyloxy.

The reaction is preferably effected in the presence of an additional base, e.g., of an alkali metal or alkaline earth metal hydroxide or carbonate, such as sodium, potassium or calcium hydroxide, or sodium, potassium or calcium carbonate, in an inert solvent, e.g., a halogenated hydrocarbon, such as dichloromethane, an ether, such as THF or dioxane, an amide, such as DMF or dimethylacetamide, or a nitrile, such as acetonitrile, at temperatures of preferably about −10°–200°, especially 0°–120°. If the leaving group E of I is different, the addition of an iodide, such as potassium iodide, is advisable.

The starting compounds of the formula II are novel, as a rule. They can be prepared, for example, by reacting a substituted aniline of the formula $R^1$—$NH_2$ with a compound of the formula $R^5CH_2$—$CHR^6$—$CH_2OH$ (where $R^5$ is E, $R^6$ is $XR^7$, $R^7$ is a protective group, or $R^5$ and $R^6$ together are also O) to give a compound of the formula $R^1$—NH—$CH_2$—$CHR^8$—$CH_2OH$ (where $R^8$ is $XR^7$ or OH), where appropriate eliminating the protective group $R^7$ to give compounds of the formula $R^1$—NH—$CH_2$—CH(XH)—$CH_2OH$, reacting with a derivative of carbonic acid, such as diethyl carbonate, to give 3-$R^1$-5-hydroxymethyl-2-oxazolidinones, and converting the hydroxymethyl group into a $CH_2E$ group, e.g., using $SOCl_2$, $SOBr_2$, methanesulfonyl chloride or p-toluenesulfonyl chloride. The compounds of the formula H—Y (III) are known, as a rule, or can be prepared in analogy with known compounds.

In addition, compounds of the formula I can be obtained by reacting a compound of the formula IV (or a reactive derivative thereof) with a reactive derivative of carbonic acid.

Suitable carbonic acid derivatives are, in particular, dialkyl carbonates, such as diethyl carbonate, and, additionally, alkyl esters of chloroformic acid, such as ethyl chloroformate. Preferably, the carbonic acid derivative, which is expediently employed in excess, also serves as a solvent or suspending agent. One of the given solvents can be present as well, provided it is inert in this reaction. Furthermore, the addition of a base is advisable, in particular of an alkali metal alcoholate, such as potassium tert-butylate. Reaction temperatures of preferably about 0°–150°, especially 70°–120°, are expediently employed.

The starting compounds of the formula IV are novel, as a rule. They can be obtained, for example, by functionalizing the abovementioned compounds of the formula $R^1$—NH—$CH_2$—CH(XH)—$CH_2OH$ to give compounds of the formula $R^1$—NH—$CH_2$—CH(XH)—$CH_2$—E and reacting with compounds of the formula H—Y (III).

In order to prepare compounds of the formula I, in which $R^1$ is a guanidinophenyl group, a corresponding aminophenyl compound can be treated with an amidinating agent. 1-Amidino-3,5-dimethylpyrazol which is, in particular, employed in the form of its nitrate, is preferred as an amidinating agent. The reaction is expediently carried out in the presence of a base, such as triethylamine or ethyl diisopropylamine, in an inert solvent or solvent mixture, e.g., water/dioxane, at temperatures of preferably about 0°–120°, especially 60°–120°.

It is furthermore possible, in a compound of the formula I, to convert one or both of the radicals $R^1$ and/or Y into (an) other radical(s) $R^1$ and/or Y.

In particular, cyano groups can be reduced to aminomethyl groups, or converted into amidino groups or hydroxyamidino groups, carboxyl groups esterified, ester groups cleaved, benzyl groups removed hydrogenolytically, and aminomethyl groups converted into guanidinomethyl groups.

Reduction of cyano groups to aminomethyl groups is expediently effected by catalytic hydrogenation, e.g., on Raney nickel at temperatures of preferably about 0°–100°, especially 10°–30°, and pressures of preferably about 1–200 bar, especially at atmospheric pressure, in an inert solvent, e.g., a lower alcohol, such as methanol or ethanol, expediently in the presence of ammonia. If the reaction is carried out, for example, at about 20° and 1 bar, benzyl ester groups or N-benzyl groups present in the starting material are then preserved. If it is desired to cleave these groups hydrogenolytically, a precious metal catalyst, preferably Pd-carbon, is then expediently used, it being possible to add an acid, such as acetic acid, and water as well, to the solution.

In order to prepare an amidine of the formula I ($R^1$= amidinophenyl), ammonia can be added onto a nitrile of the formula I ($R^1$=cyanophenyl). The addition is preferably effected in several steps, by, in a manner known per se, a) transforming the nitrile with $H_2S$ into a thioamide, which is converted with an alkylating agent, e.g., $CH_3I$, into the corresponding S-alkyl imidothio ester, which latter reacts with $NH_3$ to give the amidine, b) transforming the nitrile with an alcohol, e.g., ethanol, in the presence of HCl into the corresponding imido ester, and treating the latter with ammonia, or c) reacting the nitrile with lithium bis(trimethylsilyl)amide and subsequently hydrolyzing the product.

The corresponding N-hydroxyamidines of the formula I ($R^1$=phenyl substituted by HO—NH—C(=NH)) can be obtained from the nitriles in an analogous manner if the work is carried out according to a) or b) but using hydroxylamine in place of ammonia.

For the esterification, an acid of the formula I ($R^3$=H) can be treated with an excess of alcohol of the formula $R^3$—OH ($R^3$=A or benzyl), expediently in the presence of a strong acid, such as hydrochloric acid or sulfuric acid, at temperatures of preferably about 0°–100°, especially 20°–50°.

Conversely, an ester of the formula I ($R^3$=A or benzyl) can be converted into the corresponding acid of the formula I ($R^3$=H), expediently by solvolysis in accordance with one of the abovementioned methods, e.g. with NaOH or KOH in water/dioxane at temperatures of preferably about 0°–40°, especially 10°–30°.

A base of the formula I can be converted with an acid into the associated acid addition salt. Those acids, in particular, are suitable for this reaction which yield physiologically harmless salts. Thus, inorganic acids, e.g., sulfuric acid, nitric acid, hydrohalic acids, such as hydrochloric acid or hydrobromic acid, phosphoric acids, such as orthophosphoric acid, and sulfamic acid, and, in addition, organic acids, in particular aliphatic, alicyclic, araliphatic, aromatic or heterocyclic monobasic or polybasic carboxylic, sulfonic or sulfuric acids, e.g., formic acid, acetic acid, trifluoroacetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methanesulfonic acid or ethanesulfonic acid, ethanedisulfonic acid, 2-hydroxyethanesulfonic acid, benzenesulfonic acid, p-toluenesulfonic acid, naphthalenemonosulfonic and naphthalenedisulfonic acids, and laurylsulfuric acid, can be used. Salts with acids which are not physiologically harmless, e.g., picrates, may be used for isolating and/or purifying the compounds of the formula I.

The free bases of the formula I can, if desired, be liberated from their salts by treating with strong bases, such as sodium or potassium hydroxide, or sodium or potassium carbonate.

It is also possible to convert carboxylic acids of the formula I ($R^3$=H) into their metal or ammonium salts, e.g., their sodium, potassium or calcium salts, by reaction with corresponding bases.

The compounds of the formula I contain one or more chiral centers and can therefore be present in racemic or in optically active form. Racemates which are obtained can be resolved mechanically or chemically into the enantiomers in accordance with methods which are known per se. Preferably, diastereomers are formed from the racemic mixture by reaction with an optically active resolving agent. Suitable resolving agents are, for example, optically active acids, such as the D and L forms of tartaric acid, diacetyltartaric acid, dibenzoyltartaric acid, mandelic acid, malic acid or lactic acid, or the various optically active camphorsulfonic acids, such as β-camphorsulfonic acid. Enantiomeric resolution using a column filled with an optically active resolving agent (e.g., dinitrobenzoylphenylglycine) is also advantageous; a mixture of hexane/isopropanol/acetonitrile, e.g., in the volume ratio of 82:15:3, is an example of a suitable eluent.

Naturally, it is also possible to obtain optically active compounds of the formula I in accordance with the above-described methods by using starting compounds (e.g., those of the formula II) which are already optically active.

The novel compounds of the formula I, and their physiologically harmless salts, may be used for producing pharmaceutical preparations by bringing them into a suitable dosage form together with at least one excipient or auxiliary agent, and, if desired, together with one or more additional active compound(s). The formulations thus obtained can be employed as pharmaceuticals in human or veterinary medicine. Those organic or inorganic compounds can be used as carrier substances which are suitable for enteral (e.g., oral or rectal) or parenteral administration, or for administration in the form of an inhalation spray, and do not react with the novel compounds, for example water, vegetable oils, benzyl alcohols, polyethylene glycols, glycerol triacetate and other fatty acid glycerides, gelatin, soybean lecithin, carbohydrates, such as lactose or starch, magnesium stearate, talc and cellulose. Tablets, coated tablets, capsules, syrups, juices or drops, in particular, can be employed for oral use; lacquered tablets and capsules possessing gastric juice-resistant coatings or capsule casings are of special interest. Suppositories can be employed for rectal use, and solutions, preferably oily or aqueous solutions, and, additionally, suspensions, emulsions or implants, for parenteral administration.

For administration as an inhalation spray, sprays can be used which contain the active substance either dissolved or suspended in a propellant gas mixture. Expediently the active compound is then used in micronized form, it being possible for one or more additional physiologically tolerated solvents, e.g., ethanol, to be present. Inhalation solutions can be administered using customary inhalers. The novel compounds can also be lyophilized and the resulting lyophilizates be used, for example, for producing injection preparations. The given formulations can be sterilized and/ or contain auxiliary agents, such as preservatives, stabilizers and/or wetting agents, emulsifiers, salts for affecting the osmotic pressure, buffering substances, and colorants and/or fragrances. They may, if desired also contain one or more additional active compounds, e.g., one or more vitamins.

The substances according to the invention are administered, as a rule, in analogy with other known and commercially available pharmaceuticals, in particular, however, in analogy with the compounds described in EP-A-459256 or U.S. Pat. No. 5,232,931, preferably in dosages of about 5 mg–1 g, in particular 50–500 mg, per dosage unit. The daily dosage is preferably about 0.1–20 mg/kg, in particular 1–10 mg/kg, of body weight. However, the specific dose for each particular patient depends on a wide variety of factors, for example, the activity of the specific compound employed, on age, body weight, general health, and sex, on the food, on the time and route of administration, on the speed of excretion, on the combination of medicines employed, and on the severity of the particular disease to which the therapy applies. Oral administration is preferred.

Suitable preparations for using the compounds as antimicrobial agents are, for example, injection vials, ampoules, solutions, and capsules. Carriers, excipients, and further additive are mentioned in Examples A–E. The amount of the inventive compound in the antimicrobial agents is preferably about 0.05–500 mg per dosage unit.

In the above and that which follows, all temperatures are given in °C. in the examples below, "customary working-up" means: if necessary, water is added, pH values are adjusted to between 2 and 8 depending on the constitution of the end product, extraction takes place with ethyl acetate or dichloromethane, the phases are separated, the organic phase is dried over sodium sulfate and evaporated, and purification is then effected by chromatography on silica gel and/or by crystallization. FAB=(M$^+$+1) peak in the mass spectrum, obtained by the "fastatom bombardment" method.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German applications P 43 14 378.4, filed May 1, 1993, and P 44 05 633.8, filed Feb. 22, 1994, are hereby incorporated by reference.

EXAMPLES

Example 1

A solution of 1 g of ethyl 1-tert-butoxycarbonyl-4-(3-(4-cyanophenyl)-2-oxo-5-oxazolidinylmethyl)piperazine-2-carboxylate (obtainable by reacting 3-(4-cyanophenyl)-5-bromomethyl-2-oxazolidinone with ethyl 1-tert-butoxycarbonylpiperazine-2-carboxylate in accordance with the method described in Example 3) in 12 ml of dichloromethane and 12 ml of trifluoroacetic acid is left to stand at 20° for 1 h. and then concentrated by evaporation. Ethyl 1-(3-(4-cyanophenyl)-2-oxo-5-oxazolidinylmethyl)piperazine-3-carboxylate is obtained, FAB 359.

1-(3-(4-cyanophenyl)-2-oxo-5-oxazolidinylmethyl)piperazine-3-carboxylic acid, and its benzyl ester, is obtained in an analogous manner from 1-tert-butoxycarbonyl-4-(3-(4-cyanophenyl)-2-oxo-5-oxazolidinylmethyl)piperazine-2-carboxylic acid, or its benzyl ester.

Example 2

A solution of 1 g of tert-butyl 1-(3-(4-benzyloxycarbonylaminomethylphenyl)- 2-oxo-5-oxazolidinylmethyl)piperidine-4-oxyacetate (obtainable from 3-(4-benzyloxycarbonylaminomethylphenyl)-5-chloromethyl-2-oxazolidinone and tert-butyl piperidine-4-oxyacetate in accordance with the method described in Example 3) in a mixture of 38 ml of methanol, 6 ml of water and 6 ml of acetic acid is hydrogenated on 0.6 g of 5% Pd-carbon at 20° and 1 bar until H$_2$ uptake has ceased. The mixture is filtered and the filtrate is concentrated by evaporation, and tert-butyl 1-(3-(4-aminomethylphenyl)-2-oxo-5-oxazolidinylmethyl)piperidine- 4-oxyacetate is obtained, m.p. 95°–96°, FAB 420.

Example 3

A mixture of 2.96 g of 3-(4-cyanophenyl)-5-methanesulfonyloxymethyl-2-oxazolidinone (m.p. 162°–163°; obtainable by reacting 4-aminobenzonitrile with 2,3-epoxypropanol to give 4-(2,3-dihydroxypropylamino)benzonitrile (oily), reacting with diethyl carbonate/potassium tert-butylate at 110° to give 3-(4-cyanophenyl)-5-hydroxymemthyl-2-oxazolidinone (m.p. 130°–131°) and esterifying with methanesulfonyl chloride), 1.69 g of ethyl piperidine-4-carboxylate, 70 ml of acetonitrile, 1.38 g of potassium carbonate and 1.65 g of potassium iodide is boiled for 25 h. After customary working up, ethyl 1-(3-(4-cyanophenyl)-2-oxo-5-oxazolidinylmethyl)piperidine-4-carboxylate ("IA") is obtained, FAB 358.

The following are obtained in an analogous manner:

with benzyl piperidine-4-carboxylate:
  benzyl 1-(3-(4-cyanophenyl)-2-oxo-5-oxazolidinylmethyl)piperidine-4-carboxylate, m.p. 96°, FAB 420;

with tert-butyl piperidine-4-carboxylate:
  tert-butyl 1-(3-(4-cyanophenyl)-2-oxo-5-oxazolidinylmethyl)piperidine-4-carboxylate;

with ethyl piperidine-3-carboxylate:
  ethyl 1-(3-(4-cyanophenyl)-2-oxo-5-oxazolidinylmethyl)piperidine-3-carboxylate;

with benzyl piperidine-3-carboxylate:
  benzyl 1-(3-(4-cyanophenyl)-2-oxo-5-oxazolidinylmethyl)piperidine-3-carboxylate, FAB 420;

with tert-butyl piperidine-3-carboxylate:
  tert-butyl 1-(3-(4-cyanophenyl)-2-oxo-5-oxazolidinylmethyl)piperidine-3-carboxylate;

with ethyl piperidine-2-carboxylate:
  ethyl 1-(3-(4-cyanophenyl)-2-oxo-5-oxazolidinylmethyl)piperidine-2-carboxylate;

with benzyl piperidine-2-carboxylate:
  benzyl 1-(3-(4-cyanophenyl)-2-oxo-5-oxazolidinylmethyl)piperidine-2-carboxylate, FAB 420;

with tert-butyl piperidine-2-carboxylate:
  tert-butyl 1-(3-(4-cyanophenyl)-2-oxo-5-oxazolidinylmethyl)piperidine-2-carboxylate;

with ethyl pyrrolidine-2-carboxylate:
  ethyl 1-(3-(4-cyanophenyl)-2-oxo-5-oxazolidinylmethyl)pyrrolidine-2-carboxylate;

with benzyl pyrrolidine-2-carboxylate:
  benzyl 1-(3-(4-cyanophenyl)-2-oxo-5-oxazolidinylmethyl)pyrrolidine-2-carboxylate;

with tert-butyl pyrrolidine-2-carboxylate:
  tert-butyl 1-(3-(4-cyanophenyl)-2-oxo-5-oxazolidinylmethyl)pyrrolidine-2-carboxylate;

with ethyl piperidine-4-acetate:
  ethyl 1-(3-(4-cyanophenyl)-2-oxo-5-oxazolidinylmethyl)piperidine-4-acetate;

with benzyl piperidine-4-acetate:
  benzyl 1-(3-(4-cyanophenyl)-2-oxo-5-oxazolidinylmethyl)piperidine-4-acetate;

with tert-butyl piperidine-4-acetate:
  tert-butyl 1-(3-(4-cyanophenyl)-2-oxo-5-oxazolidinylmethyl)piperidine-4-acetate;

with ethyl piperidine-4-oxyacetate:
  ethyl 1-(3-(4-cyanophenyl)-2-oxo-5-oxazolidinylmethyl)piperidine-4-oxyacetate;

with benzyl piperidine-4-oxyacetate:
  benzyl 1-(3-(4-cyanophenyl)-2-oxo-5-oxazolidinylmethyl)piperidine-4-oxyacetate;

with tert-butyl piperidine-4-oxyacetate:
  tert-butyl 1-(3-(4-cyanophenyl)-2-oxo-5-oxazolidinylmethyl)piperidine-4-oxyacetate, m.p. 88°–89°; FAB 416;

with ethyl piperidine-3-oxyacetate:
  ethyl 1-(3-(4-cyanophenyl)-2-oxo-5-oxazolidinylmethyl)piperidine-3-oxyacetate;

with benzyl piperidine-3-oxyacetate:
  benzyl 1-(3-(4-cyanophenyl)-2-oxo-5-oxazolidinylmethyl)piperidine-3-oxyacetate;

with tert-butyl piperidine-3-oxyacetate:
  tert-butyl 1-(3-(4-cyanophenyl)-2-oxo-5-oxazolidinylmethyl)piperidine-3-oxyacetate;

with ethyl piperazine-1-acetate:
  ethyl 1-(3-(4-cyanophenyl)-2-oxo-5-oxazolidinylmethyl)piperazine-4-acetate;

with benzyl piperazine-1-acetate:
  benzyl 1-(3-(4-cyanophenyl)-2-oxo-5-oxazolidinylmethyl)piperazine-4-acetate;

with tert-butyl piperazine-1-acetate:
  tert-butyl 1-(3-(4-cyanophenyl)-2-oxo-5-oxazolidinylmethyl)piperazine-4-acetate;

with ethyl azetidine-3-oxyacetate:
  ethyl 1-(3-(4-cyanophenyl)-2-oxo-5-oxazolidinylmethyl)azetidine-3-oxyacetate;

with benzyl azetidine-3-oxyacetate:
  benzyl 1-(3-(4-cyanophenyl)-2-oxo-5-oxazolidinylmethyl)azetidine-3-oxyacetate;

with tert-butyl azetidine-3-oxyacetate:
  tert-butyl 1-(3-(4-cyanophenyl)-2-oxo-5-oxazolidinylmethyl)azetidine-3-oxyacetate;

with ethyl 1-benzylpiperazine-2-carboxylate:
  ethyl 1-benzyl-4-(3-(4-cyanophenyl)-2-oxo-5-oxazolidinyl)piperazine-2-carboxylate;

with benzyl 1-benzylpiperazine-2-carboxylate:
  benzyl 1-benzyl-4-(3-(4-cyanophenyl)-2-oxo-5-oxazolidinyl)piperazine-2-carboxylate;

with tert-butyl 1-benzylpiperazine-2-carboxylate:
  tert-butyl 1-benzyl-4-(3-(4-cyanophenyl)-2-oxo-5-oxazolidinyl)piperazine-2-carboxylate.

The following is obtained in an analogous manner by the reaction of 3-(4-cyanophenyl)-5S-methanesulfonyloxymethyl-2-oxazolidinone (m.p. 141°–142°; $[\alpha]_D^{20}$ +75.3° (c=3.9 mg/ml in methanol); obtainable by reacting 4-aminobenzonitrile with 2R-2,3-epoxypropanol to give 4-(2S,3-dihydroxypropylamino)benzonitrile, reacting with diethyl carbonate/potassium tert-butylate to give 3-(4-cyanophenyl)-5S-hydroxymethyl-2-oxazolidinone and esterifying with methanesulfonyl chloride) with benzyl piperidine-4-carboxylate: benzyl 1-(3-(4-cyanophenyl)-2-oxo-5S-oxazolidinylmethyl)piperidine-4-carboxylate, m.p 87°–88°, $[\alpha]_D^{20}$ 43.0° (c=9.8 mg/ml in methanol).

The following are obtained in an analogous manner with ethyl piperidine-4-carboxylate:
  ethyl 1-(3-(4-cyanophenyl)-2-oxo-5S-oxazolidinylmethyl)piperidine-4-carboxylate;

with tert-butyl piperidine-4-carboxylate:
  tert-butyl 1-(3-(4-cyanophenyl)-2-oxo-5S-oxazolidinylmethyl)piperidine-4-carboxylate.

Benzyl 1-(3-(4-cyanophenyl)-2-oxo-5R-oxazolidinylmethyl)piperidine-4-carboxylate and the corresponding ethyl ester and the corresponding tert-butyl ester are obtained in an analogous manner from 3-(4-cyanophenyl)-5R-methanesulfonyloxymethyl-2-oxazolidinone (obtainable from 2S-2,3-epoxypropanol via 4-(2R,3-dihydroxypropylamino)benzonitrile and 3-(4-cyanophenyl)-5R-hydroxymethyl-2-oxazolidinone).

Example 4

In analogy with Example 3, tert-butyl 1-(3-(4-dimethylaminomethylphenyl)-2-oxo-5-oxazolidinylmethyl)piperidine-4-carboxylate, FAB 432, is obtained from the reaction of 3-(4-dimethylaminomethylphenyl)-5-bromomethyl-2-oxazolidinone (obtainable by reacting 4-dimethylaminomethylaniline with 2,3-epoxypropanol to give 3-(4-dimethylaminomethylphenylamino)-1,2-propanediol, reacting with diethyl carbonate/potassium tertbutylate to give 3-(4-dimethylaminomethylphenyl)5-hydroxymethyl-2-oxazolidinone and reacting with $SOBr_2$) with tert-butyl piperidine-4-carboxylate.

Example 5

A mixture of 3.31 g of ethyl 1-(3-(4-cyanophenyl)-2-hydroxypropyl)piperidine-4-carboxylate (obtainable by reacting 3-(4-cyanophenyl)-1,2-propanediol1-methanesulfonate with ethyl piperidine-4-carboxylate), 15 ml of diethyl carbonate and 0.1 g of potassium tertbutylate is stirred at a bath temperature of 110° for 2 h. The mixture is concentrated by evaporation, worked up in the customary manner, and "IA", FAB 358, is obtained.

Example 6

0.17 ml of ethyl diisopropylamine is added to a solution of 201 mg of 1-amidino-3,5-dimethylpyrazole nitrate in 17 ml of dioxane and 5 ml of water and the mixture is stirred for 15 min. 375 mg of tert-butyl 1-(3-(4-aminophenyl)-2-oxo-5-oxazolidinylmethyl)piperidine-4-carboxylate (obtainable by reacting 4-aminoacetanilide with 2,3-epoxypropanol to give 4-(2,3-dihydroxypropylamino)acetanilide, reacting with diethyl carbonate to give 3-(4-acetamidophenyl)-5-hydroxymethyl-2-oxazolidinone, converting into the methanesulfonate and reacting with tert-butyl piperidine-4-carboxylate) are then added, and the mixture is then boiled for 45 h., concentrated by evaporation and worked up in the customary manner, and tert-butyl 1-(3-(4-guanidinophenyl)-2-oxo-5-oxazolidinylmethyl)piperidine-4-carboxylate is obtained.

tert-Butyl 1-(3-(4-guanidinomethylphenyl)-2-oxo-5-oxazolidinylmethyl)piperidine-4-carboxylate, FAB 432, is obtained in an analogous manner from the reaction of tert-butyl 1-(3-(4-aminomethylphenyl)-2-oxo-5-oxazolidinylmethyl)piperidine-4-carboxylate and 1-amidino-3,5-dimethylpyrazole nitrate.

Example 7

A solution of 1 g of "IA" in 40 ml of 10% methanolic $NH_3$ solution is hydrogenated on 0.6 g of Raney Ni at 20° and 1 bar until $H_2$ uptake is complete. Following filtration and concentration by evaporation, ethyl 1-(3-(4-aminomethylphenyl)-2-oxo-5-oxazolidinylmethyl)piperidine-4-carboxylate, FAB 362, is obtained.

The following 1-(3-(4-aminomethylphenyl)-2-oxo-5-oxazolidinylmethyl)piperidines are obtained in an analogous manner by hydrogenating the corresponding nitriles:

-4-carboxylic acid tert-butyl ester
-3-carboxylic acid ethyl ester
-3-carboxylic acid tert-butyl ester
-2-carboxylic acid ethyl ester
-2-carboxylic acid tert-butyl ester
-4-acetic acid ethyl ester
-4-acetic acid tert-butyl ester
-4-oxyacetic acid ethyl ester
-4-oxyacetic acid tert-butyl ester, m.p. 95°–96°, FAB 420
-3-oxyacetic acid ethyl ester
-3-oxyacetic acid tert-butyl ester;

as are the following 1-(3-(4-aminomethylphenyl)-2-oxo-5-oxazolidinylmethyl)pyrrolidines:

-2-carboxylic acid ethyl ester
-2-carboxylic acid tert-butyl ester;

as are the following 1-(3-(4-aminomethylphenyl)-2-oxo-5-oxazolidinylmethyl)piperazines:

-4-acetic acid ethyl ester
-4-acetic acid tert-butyl ester;

as are the following 1-(3-(4-aminomethylphenyl)-2-oxo-5-oxazolidinylmethyl)azetidines:

-3-oxyacetic acid ethyl ester
-3-oxyacetic acid tert-butyl ester;

as are the following 1-(3-(4-aminomethylphenyl)-2-oxo-5-oxazolidinylmethyl)-4-benzylpiperazines:

-3-carboxylic acid ethyl ester
-3-carboxylic acid tert-butyl ester;

as are the following 1-(3-(4-aminomethylphenyl)-2-oxo-5S-oxazolidinylmethyl)piperidines:

-4-carboxylic acid ethyl ester
-4-carboxylic acid tert-butyl ester;

as are the following 1-(3-(4-aminomethylphenyl)-2-oxo-5R-oxazolidinylmethyl)piperidines:

-4-carboxylic acid ethyl ester
-4-carboxylic acid tert-butyl ester.

Example 8

$H_2S$ is passed (45 min) at –10° into a solution of 3.57 g of "IA" in 50 ml of pyridine and 6.6 ml of triethylamine. Subsequently, the mixture is stirred at 20° for 14 h and then concentrated by evaporation; the residue is dissolved in 50 ml of acetone and 9 ml of methyl iodide are added to this solution. After stirring at 20° for 6 hours, filtering off takes place and the residue is washed with a little acetone and dissolved in 30 ml of methanol; 4.6 g of ammonium acetate are then added and the mixture is stirred at 20° for 30 h. The resulting ethyl 1-(3-(4-amidinophenyl)-2-oxo-5-oxazolidinylmethyl)piperidine-4-carboxylate is filtered off and chromatographed on silica gel (dichloromethane/methanol/acetic acid 70:30:2); m.p. 200° (decomp.); FAB 375.

The following 1-(3-(4-amidinophenyl)-2-oxo-5-oxazolidinylmethyl)piperidines are obtained in an analogous manner from the corresponding nitriles:

-4-carboxylic acid benzyl ester, m.p. 204° (decomp.); FAB 437; dihydrochloride m.p. 182°
-4-carboxylic acid tert-butyl ester
-3-carboxylic acid ethyl ester
-3-carboxylic acid benzyl ester, acetate, FAB 437
-3-carboxylic acid tert-butyl ester
-2-carboxylic acid ethyl ester
-2-carboxylic acid benzyl ester, FAB 437
-2-carboxylic acid tert-butyl ester
-4-acetic acid ethyl ester
-4-acetic acid benzyl ester -4-acetic acid tert-butyl ester -4-oxyacetic acid ethyl ester -4-oxyacetic acid benzyl ester, acetate, m.p. 206°

-4-oxyacetic acid tert-butyl ester, m.p. 187° (decomp.); FAB 433

-3-oxyacetic acid ethyl ester

-3-oxyacetic acid benzyl ester

-3-oxyacetic acid tert-butyl ester;

as are the following 1-(3-(4-amidinophenyl)-2-oxo-5-oxazolidinylmethyl)pyrrolidines:

-2-carboxylic acid ethyl ester

-2-carboxylic acid benzyl ester

-2-carboxylic acid tert-butyl ester;

as are the following 1-(3-(4-amidinophenyl)-2-oxo-5-oxazolidinylmethyl)piperazines:

-4-acetic acid ethyl ester

-4-acetic acid benzyl ester, FAB 452

-4-acetic acid tert-butyl ester;

as are the following 1-(3-(4-amidinophenyl)-2-oxo-5-oxazolidinylmethyl)azetidines:

-3-oxyacetic acid ethyl ester

-3-oxyacetic acid benzyl ester

-3-oxyacetic acid tert-butyl ester;

as are the following 1-(3-(4-amidinophenyl)-2-oxo-5-oxazolidinylmethyl)-4-benzylpiperazines:

-3-carboxylic acid ethyl ester

-3-carboxylic acid benzyl ester

-3-carboxylic acid tert-butyl ester;

as are the following 1-(3-(4-amidinophenyl)-2-oxo-5S-oxazolidinylmethyl)piperidines:

-4-carboxylic acid ethyl ester

-4-carboxylic acid benzyl ester

-4-carboxylic acid tert-butyl ester;

as are the following 1-(3-(4-amidinophenyl)-2-oxo-5R-oxazolidinylmethyl)piperidines:

-4-carboxylic acid ethyl ester

-4-carboxylic acid benzyl ester

-4-carboxylic acid tert-butyl ester.

Example 9

Ethyl 1-(3-(4-hydroxyamidinophenyl)-2-oxo-5-oxazolidinylmethyl)piperidine-4-carboxylate is obtained from "IA" in analogy with Example 8, but using an equivalent quantity of hydroxylammonium acetate instead of ammonium acetate.

Example 10

1 g of tert-butyl (1-(3-(4-cyanophenyl)-2-oxo-5-oxazolidinylmethyl)piperidine-4-carboxylate is dissolved in 12 ml of dichloromethane, and 12 ml of trifluoroacetic acid are then added; the mixture is left to stand for 5 min., concentrated by evaporation and worked up in the customary manner; 1-(3-(4-cyanophenyl)-2-oxo-5-oxazolidinylmethyl)piperidine-4-carboxylic acid, FAB 330, is obtained.

The following acids are obtained in an analogous manner from the corresponding tert-butyl esters:

1-(3-(4-cyanophenyl)-2-oxo-5-oxazolidinylmethyl)piperidine-3-carboxylic acid 1-(3-(4-cyanophenyl)-2-oxo-5-oxazolidinylmethyl)piperidine-2-carboxylic acid 1-(3-(4-cyanophenyl)-2-oxo-5-oxazolidinylmethyl)pyrrolidine-2-carboxylic acid 1-(3-(4-cyanophenyl)-2-oxo-5-oxazolidinylmethyl)piperidine-4-acetic acid 1-(3-(4-cyanophenyl)-2-oxo-5-oxazolidinylmethyl)piperidine-4-oxyacetic acid 1-(3-(4-cyanophenyl)-2-oxo-5-oxazolidinylmethyl)piperidine-3-oxyacetic acid 1-(3-(4-cyanophenyl)-2-oxo-5-oxazolidinylmethyl)piperazine-4-acetic acid 1-(3-(4-cyanophenyl)-2-oxo-5-oxazolidinylmethyl)azetidine-3-oxyacetic acid 1-benzyl-4-(3-(4-cyanophenyl)-2-oxo-5-oxazolidinylmethyl)piperazine-2-carboxylic acid 1-(3-(4-aminomethylphenyl)-2-oxo-5-oxazolidinylmethyl)piperidine-4-carboxylic acid, m.p. 190° (decomp.); FAB 334

1-(3-(4-aminomethylphenyl)-2-oxo-5-oxazolidinylmethyl)piperidine-3-carboxylic acid 1-(3-(4-aminomethylphenyl)-2-oxo-5-oxazolidinylmethyl)piperidine-2-carboxylic acid 1-(3-(4-aminomethylphenyl)-2-oxo-5-oxazolidinylmethyl)pyrrolidine-2-carboxylic acid 1-(3-(4-aminomethylphenyl)-2-oxo-5-oxazolidinylmethyl)piperidine-4-acetic acid 1-(3-(4-aminomethylphenyl)-2-oxo-5-oxazolidinylmethyl)piperidine-4-oxyacetic acid, m.p. 135°; FAB 364

1-(3-(4-aminomethylphenyl)-2-oxo-5-oxazolidinylmethyl)piperidine-3-oxyacetic acid 1-(3-(4-aminomethylphenyl)-2-oxo-5-oxazolidinylmethyl)piperazine-4-acetic acid 1-(3-(4-aminomethylphenyl)-2-oxo-5-oxazolidinylmethyl)azetidine-3-oxyacetic acid 1-benzyl-4-(3-(4-aminomethylphenyl)-2-oxo-5-oxazolidinylmethyl)piperazine-2-carboxylic acid 1-(3-(4-amidinophenyl)-2-oxo-5-oxazolidinylmethyl)piperidine-4-carboxylic acid, m.p. 265° (decomp.); FAB 347; dihydrochloride, m.p. 142°

1-(3-(4-amidinophenyl)-2-oxo-5-oxazolidinylmethyl)piperidine-3-carboxylic acid 1-(3-(4-amidinophenyl)-2-oxo-5-oxazolidinylmethyl)piperidine-2-carboxylic acid, m.p. 198°; FAB 347

1-(3-(4-amidinophenyl)-2-oxo-5-oxazolidinylmethyl)pyrrolidine-2-carboxylic acid 1-(3-(4-amidinophenyl)-2-oxo-5-oxazolidinylmethyl)piperidine-4-acetic acid, m.p. 256°

1-(3-(4-amidinophenyl)-2-oxo-5-oxazolidinylmethyl)piperidine-4-oxyacetic acid, oil, FAB 377

1-(3-(4-amidinophenyl)-2-oxo-5-oxazolidinylmethyl)piperidine-3-oxyacetic acid, m.p. 167°–168°

1-(3-(4-amidinophenyl)-2-oxo-5-oxazolidinylmethyl)piperazine-4-acetic acid, FAB 362

1-(3-(4-amidinophenyl)-2-oxo-5-oxazolidinylmethyl)azetidine-3-oxyacetic acid 1-benzyl-4-(3-(4-amidinophenyl)-2-oxo-5-oxazolidinylmethyl)piperazine-2-carboxylic acid 1-(3-(4-guanidinophenyl)-2-oxo-5-oxazolidinylmethyl)piperidine-4-carboxylic acid 1-(3-(4-guanidinomethylphenyl)-2-oxo-5-oxazolidinylmethyl)piperidine-4-carboxylic acid, FAB 376

1-(3-(4-cyanophenyl)-2-oxo-5S-oxazolidinylmethyl)piperidine-4-carboxylic acid 1-(3-(4-cyanophenyl)-2-oxo-5R-oxazolidinylmethyl)piperidine-4-carboxylic acid 1-(3-(4-aminomethylphenyl)-2-oxo-5S-oxazolidinylmethyl)piperidine-4-carboxylic acid 1-(3-(4-aminomethylphenyl)-2-oxo-5R-oxazolidinylmethyl)piperidine-4-carboxylic acid 1-(3-(4-amidinomethylphenyl)-2-oxo-5S-oxazolidinylmethyl)piperidine-4-carboxylic acid 1-(3-(4-amidinomethylphenyl)-2-oxo-5R-oxazolidinylmethyl)piperidine-4-carboxylic acid 1-(3-(4-dimethylaminomethylphenyl)-2-oxo-5-oxazolidinylmethyl)piperidine-4-carboxylic acid.

Example 11

A solution of 1 g of benzyl 1-(3-(4-amidinophenyl)-2-oxo-5-oxazolidinylmethyl)piperidine-4-carboxylate in 100 ml of methanol, 17 ml of acetic acid and 17 ml of water is hydrogenated on 0.7 g of 5% Pd-carbon at 20° and 1 bar until hydrogen uptake has ceased. The mixture is filtered and concentrated by evaporation, and the residue is triturated with diethyl ether, with 1-(3-(4-amidinophenyl)-2-oxo-5-oxazolidinylmethyl)piperidine-4-carboxylic acid being obtained, m.p. 265°; FAB 347; dihydrochloride, m.p. 142°.

Example 12

1-(3-(4-Aminomethylphenyl)-2-oxo-5-oxazolidinylmethyl)piperazine-3-carboxylic acid is obtained in analogy with Example 11 by the hydrogenation of 1-benzyl-4-(3-(4-cyanophenyl)-2-oxo-5-oxazolidinylmethyl)piperazine-2-carboxylic acid ("IB"; or of "IB" benzyl ester).

The same substance can be obtained in an analogous manner by the hydrogenation of 1-benzyl-4-(3-(4-aminomethylphenyl)-2-oxo-5-oxazolidinylmethyl)piperazine-2-carboxylic acid (or of its benzyl ester).

Ethyl 1-(3-(4-aminomethylphenyl)-2-oxo-5-oxazolidinylmethyl)piperazine-3-carboxylate and tert-butyl 1-(3-(4-aminomethylphenyl)-2-oxo-5-oxazolidinylmethyl)piperazine-3-carboxylate are obtained in an analogous manner from the ethyl and tert-butyl esters of "IB", respectively.

Example 13

The following are obtained by analogy with Example 3 from 3-(4-cyanophenyl)-5-methanesulfonyloxymethyl-2-oxazolidinone:

with benzyl piperidine-3-acetate:
benzyl 1-(3-(4-cyanophenyl)-2-oxo-5-oxazolidinylmethyl)piperidine-3-acetate, FAB 434 with methyl 3-(1-piperazinyl)propionate:
methyl 3-(4-(3-(4-cyanophenyl)-2-oxo-5-oxazolidinylmethyl)-1-piperazinyl)propionate, FAB 373 with ethyl 3-(1-piperazinyl)propionate:
ethyl 3-(4-(3-(4-cyanophenyl)-2-oxo-5-oxazolidinylmethyl)-1-piperazinyl)propionate, FAB 387 with ethyl 2-oxopiperazin-1-acetate:
ethyl 1-(3-(4-cyanophenyl)-2-oxo-5-oxazolidinylmethyl)-3-oxo-piperazine-4-acetate, FAB 387 with ethyl 3-(2-oxo-1-piperazinyl)propionate:
ethyl 3-(4-(3-(4-cyanophenyl)-2-oxo-5-oxazolidinylmethyl)-2-oxo-1-piperazinyl)-propionate, FAB 401 with ethyl 4-hydroxypiperidine-4-carboxylate:
ethyl 1-(3-(4-cyanophenyl)-2-oxo-5-oxazolidinylmethyl)-4-hydroxypiperidine-4-carboxylate, FAB 374 with ethyl 4-hydroxypiperidine-4-acetate:
ethyl 1-(3-(4-cyanophenyl)-2-oxo-5-oxazolidinylmethyl)- 4-hydroxypiperidine-4-acetate, FAB 388 with 1-oxa-8-azaspiro[4.5]decan-2-one (=lactone of 3-(4-hydroxy-4-piperidyl)propionic acid):
8-(3-(4-cyanophenyl)-2-oxo-5-oxazolidinylmethyl)-1-oxa-8-azaspiro[4.5]decan-2-one, FAB 356. The following are obtained analogously from 3-(4-cyanophenyl)-5R- or -5S-methanesulfonyloxymethyl-2-oxazolidinone:

with benzyl piperidine-4-carboxylate:
benzyl 1-(3-(4-cyanophenyl)-2-oxo-5R-oxazolidinylmethyl)piperidine-4-carboxylate benzyl 1-(3-(4-cyanophenyl)-2-oxo-5S-oxazolidinylmethyl)piperidine-4-carboxylate with ethyl piperazine-4-acetate:
ethyl 1-(3-(4-cyanophenyl)-2-oxo-5R-oxazolidinylmethyl)piperazine-4-acetate, FAB 373 ethyl 1-(3-(4-cyanophenyl)-2-oxo-5S-oxazolidinylmethyl)piperazine-4-acetate, FAB 373 with benzyl 3-(1-piperazinyl)propionate
benzyl 3-(4-(3-(4-cyanophenyl)-2-oxo-5R-oxazolidinylmethyl)-1-piperazinyl)propionate, m.p. 90° benzyl 3-(4-(3-(4-cyanophenyl)-2-oxo-5S-oxazolidinylmethyl)-1-piperazinyl)propionate, m.p. 90°.

Example 14

The following are obtained by analogy with Example 8 from the corresponding nitriles (see Example 13):

benzyl 1-(3-(4-amidinophenyl)-2-oxo-5-oxazolidinylmethyl)piperidine-3-acetate, diacetate, m.p. 287°–288° ethyl 3-(4-(3-(4-amidinophenyl)-2-oxo-5-oxazolidinylmethyl)-1-piperazinyl)propionate, m.p. 206° ethyl 1-(3-(4-amidinophenyl)-2-oxo-5-oxazolidinylmethyl)-3-oxo-piperazine-4-acetat, m.p. 224° ethyl 3-(4-(3-(4-amidinophenyl)-2-oxo-5-oxazolidinylmethyl)-2-oxo-1-piperazinyl)propionate, FAB 418 ethyl 1-(3-(4-amidinophenyl)-2-oxo-5-oxazolidinylmethyl)-4-hydroxypiperidine-4-carboxylate ethyl 1-(3-(4-amidinophenyl)-2-oxo-5-oxazolidinylmethyl)-4-hydroxypiperidine-4-acetate, acetate, m.p. 108°

8-(3-(4-amidinophenyl)-2-oxo-5-oxazolidinylmethyl)-1-oxa-8-azaspiro-[4.5]decan-2-one, FAB 373 benzyl 1-(3-(4-amidinophenyl)-2-oxo-5R-oxazolidinylmethyl)piperidine-4-carboxylate, acetate, m.p. 225° $[\alpha]_D^{20}$ +40.5° (c=1, methanol)

benzyl 1-(3-(4-amidinophenyl)-2-oxo-5S-oxazolidinylmethyl)piperidine-4-carboxylate, acetate, m.p. 225° $[\alpha]_D^{20}$ −41° (c=1, methanol)

ethyl 1-(3-(4-amidinophenyl)-2-oxo-5R-oxazolidinylmethyl)piperazine-4-acetate, FAB 390 ethyl 1-(3-(4-amidinophenyl)-2-oxo-5S -oxazolidinylmethyl)piperazine-4-acetate, FAB 390.

Example 15

The following are obtained by analogy with Example 9 from the corresponding nitriles:

ethyl 1-(3-(4-hydroxyamidinophenyl)-2-oxo-5-oxazolidinylmethyl)-4-hydroxypiperidine-4-acetate, acetate, m.p. 178°–180° methyl 3-(4-(3-(4-hydroxyamidinophenyl)-2-oxo-5oxazolidinylmethyl)-1-piperazinyl)propionate, m.p. 202° benzyl 3-(4-(3-(4-hydroxyamidinophenyl)-2-oxo-5-oxazolidinylmethyl)-1-piperazinyl)propionate, m.p. 159° benzyl 3-(4-(3-(4-hydroxyamidinophenyl)-2-oxo-5-oxazolidinylmethyl)-1-piperazinyl)propionate, m.p. 159°

Example 16

A mixture of 1 g of ethyl 3-(4-(3-(4-amidinophenyl)-2-oxo-5-oxazolidinylmethyl)-1-piperazinyl)propionate, 0.2 g of NaOH, 8 ml of dioxane and 2 ml of water is stirred at 20° for 5 hours. After acidification and conventional work-up, 3-(4-(3-(4-amidinophenyl)-2-oxo-5oxazolidinylmethyl)-1-piperazinyl)propionic acid m.p. 269°, is obtained The following are obtained analogously by hydrolysis of the corresponding esters:

1-(3-(4-amidinophenyl)-2-oxo-5-oxazolidinylmethyl)3-oxo-piperazine-4-acetic acid, monohydrate, m.p. 261°

3-(4-(3-(4-amidinophenyl)-2-oxo-5-oxazolidinylmethyl)-2-oxo-1-piperazinyl)propionic acid, FAB 390

1-(3-(4-amidinophenyl)-2-oxo-5-oxazolidinylmethyl)-4-hydroxypiperidine-4-carboxylic acid 1-(3-(4-amidinophenyl)-2-oxo-5-oxazolidinylmethyl)-4-hydroxypiperidine-4-acetic acid, m.p. 230°

1-(3-(4-amidinophenyl)-2-oxo-5R-oxazolidinylmethyl)piperazine-4-acetic acid, acetate, FAB 362, $[\alpha]_D^{20}$ −28.0° (c=1, DMSO)

1-(3-(4-amidinophenyl)-2-oxo-5S -oxazolidinylmethyl)piperazine-4-acetic acid, acetate, FAB 362, $[\alpha]_D^{20}$ +24.0° (c=1, DMSO)

Example 17 a) 1 g of ethyl 1-(3-(4-cyanophenyl)-2-oxo-5-oxazolidinylmethyl)-4-methanesulfonyloxypiperidine-4-acetate (obtainable from the 4-hydroxy compound (see Example 13) with methanesulfonyl chloride/pyridine) is dissolved in a 2% $NH_3$ solution in 10 ml of a 1:1 mixture of ethanol and THF, and the solution is left to stand at 20° for 2 hours. The solution is concentrated by evaporation and subjected to conventional work-up to give ethyl 1-(3-(4-cyanophenyl)-2-oxo-5-oxazolidinylmethyl)-4-aminopiperidine-4-acetate, FAB 387.

b) By analogy with Example 8, ethyl 1-(3-(4-amidinophenyl)-2-oxo-5-oxazolidinylmethyl)-4-aminopiperidine-4-acetate, FAB 404, is obtained therefrom.

c) By analogy with Example 16, 1-(3-(4-amidinophenyl)-2-oxo-5-oxazolidinylmethyl)-4-aminopiperidine-4-acetic acid, FAB 376, is obtained therefrom by hydrolysis.

Example 18 a) By analogy with Example 17a), from ethyl 1-(3-(4-cyanophenyl)-2-oxo-5-oxazolidinylmethyl)-4-methanesulfonyloxypiperidine-4-carboxylate (obtainable from the 4-hydroxy compound (see Example 13) with methanesulfonyl chloride/pyridine) with $NH_3$, ethyl 1-(3-(4-cyanophenyl)-2-oxo-5-oxazolidinylmethyl)-4-aminopiperidine-4-carboxylate, FAB 373, is obtained.

b) By analogy with Example 8, ethyl 1-(3-(4-amidinophenyl)-2-oxo-5-oxazolidinylmethyl)-4-aminopiperidine-4-carboxylate, FAB 390, is obtained therefrom.

c) By analogy with Example 16, 1-(3-(4-amidinophenyl)-2-oxo-5-oxazolidinylmethyl)-4-aminopiperidine-4-carboxylic acid, FAB 362, is obtained therefrom by hydrolysis.

Example 19

A solution of 1 g of benzyl 3-(4-(3-(4-hydroxyamidinophenyl)-2-oxo-5R- or -5S-oxazolidinylmethyl)-1-piperazinyl)propionate (see Example 15) in 30 ml of acetic acid, with the addition of 1 ml of acetic anhydride, is hydrogenated over 0.2 g of 10% Pd-C at 20° and 1 bar, until the calculated quantity of hydrogen has been taken up. The mixture is filtered and subjected to conventional work-up to give:

3-(4-(3-(4-Amidinophenyl)-2-oxo-5R-oxazolidinylmethyl)-1-piperazinyl)propionic acid, acetate, m.p. 200°–220° (decomp.), $[\alpha]_D^{20}$ +9° (c=0.5, DMSO) or 3-(4-(3-(4-Amidinophenyl)-2-oxo-5S-oxazolidinylmethyl)-1-piperazinyl)propionic acid, acetate, m.p. 200°–220° (decomp.), $[\alpha]_D^{20}$ −8° (c=0.5, DMSO).

The following examples relate to pharmaceutical formulations.

Example A: Tablets

A mixture of 1 kg of active compound of the formula I, 4 kg of lactose, 1.2 kg of corn starch, 200 g of talc and 100 g of magnesium stearate is compressed in the customary manner to form tablets such that each tablet contains 100 mg of active compound.

Example B: Coated tablets

Tablets are moulded in analogy with Example A, which tablets are then coated, in a customary manner, with a coating consisting of sucrose, corn starch, talc, tragacanth and colorant.

Example C: Capsules

Hard gelatin capsules are filled, in a customary manner, with 500 g of active compound of the formula I such that each capsule contains 500 mg of active compound.

Example D: Injection vials

A solution of 100 g of active compound of the formula I in 4 l of doubly-distilled water is adjusted to pH 6.5 with 2N hydrochloric acid and filtered to render it sterile, and then used to fill injection vials. The vial contents are lyophilized, and the vials then sealed, under sterile conditions. Each injection vial contains 50 mg of active compound.

Example E: Suppositories

A mixture of 50 g of active compound of the formula I together with 10 g of soybean lecithin and 140 g of cacao butter is melted and then poured into moulds and allowed to cool. Each suppository contains 250 mg of active compound.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the formula I

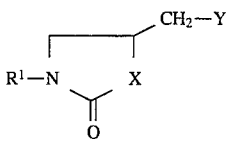

wherein

X is O;

Y is aziridino, azetidino, pyrrolidino, piperidino, 1-oxa-8-azaspiro[4.5]dec-8yl, hexahydroazepino or 4-$R^4$-piperazino which is unsubstituted or substituted once by $R^2$, OZ, SZ, $N(Z)_2$ or -oxo;

Z is in each case H, A, phenyl-$C_kH_{2k}$ or Ac;

$R^1$ is phenyl which is substituted once by CN, $H_2N$—$CH_2$—, $(A)_2N$—$CH_2$—, $H_2N$—$C(=NH)$—, $H_2N$—$C(=NH)$—NH—, $H_2N$—$C(=NH)$—NH—$CH_2$—, HO—NH—$C(=NH)$— or HO—NH—$C(=NH)$—NH—;

$R^2$ is —$C_mH_{2m}$—$COOR^3$ or —$C_nH_{2n}$—O—$C_pH_{2p}$—$COOR^3$;

$R^3$ is H, A or benzyl;

$R^4$ is H, A, benzyl or —$C_mH_{2m}$—$COOR^3$;

A is in each case alkyl having 1–6 C atoms;

Ac is carboxylic acyl having 1–11 C atoms;

k and m are in each case independently 0, 1, 2 or 3;

n is 0, 1 or 2; and p is 1, 2 or 3; or a salt thereof.

2. A compound according to claim 1, wherein A is alkyl of 1–4 C atoms.

3. A compound according to claim 1, wherein Y is 3-($R^3OOC$)-azetidino, 3-($R^3OOC$—$CH_2$—O—)-azetidino, 2-($R^3OOC$—)-pyrrolidino, 3-($R^3OOC$—)-pyrrolidino, 2-($R^3OOC$—)-piperidino, 3-($R^3OOC$—)-piperidino, 4-($R^3OOC$—)-piperidino, 2-($R^3OOC$—$CH_2$—)-piperidino, 4-($R^3OOC$—$CH_2CH_2$—)-piperidino, 4-hydroxy-4-($R^3OOC$)-piperidino, 4-hydroxy-4-($R^3OOC$—$CH_2$—)-piperidino, 4-amino-4-($R^3OOC$)-piperidino, 4-amino-4-($R^3OOC$—$CH_2$—)-piperidino, 3-oxo-4-($R^3OOC$—$CH_2$—)-piperidino, 2-($R^3OOC$—$CH_2$—O—)-piperidino, 3-($R^3OOC$—$CH_2$—O—)-piperidino, 4-($R^3OOC$—$CH_2$—O—)-piperidino, 1-oxa-2-oxo-8-azaspiro[4.5]dec-8-yl, 2-, 3- or 4-($R^3OOC$)-hexahydroazepino, 4-($R^3OOC$—$CH_2$—)-piperazino, 3-($R^3OOC$)-piperazino, or 4-benzyl-3-($R^3OOC$)-piperazino.

4. A compound according to claim 1, wherein Z is H, A, phenyl, benzyl, acetyl or benzoyl.

5. A compound according to claim 1, wherein $R^1$ is 2-cyanophenyl, 3-cyanophenyl, 4-cyanophenyl, 2-aminomethylphenyl, 3-aminomethylphenyl, 4-aminomethylphenyl, 2-dimethylaminomethylphenyl, 3-dimethylaminomethylphenyl, 4-dimethylaminomethylphenyl, 2-amidinophenyl, 3-amidinophenyl, 4-amidinophenyl, 2-guanidinophenyl, 3-guanidinophenyl, 4-guanidinophenyl, 2-guanidinomethylphenyl, 3-guanidinomethylphenyl, 4-guanidinomethylphenyl, 2-hydroxyamidinophenyl, 3-hydroxyamidinophenyl or 4-hydroxyamidinophenyl.

6. A compound according to claim 5, wherein $R^1$ is 4-cyanophenyl, 4-aminomethylphenyl, 4-dimethylaminomethylphenyl, 4-amidinophenyl, 4-guanidinophenyl, 4-guanidinomethylphenyl or 4-hydroxyamidinophenyl.

7. A compound according to claim 1, wherein $R^2$ is —$COOR^3$, —$CH_2COOR^3$ or —O—$CH_2COOR^3$.

8. A compound according to claim 1, wherein $R^3$ is H, methyl, ethyl, tert-butyl or benzyl.

9. A compound according to claim 1, wherein $R^1$ is cyanophenyl.

10. A compound according to claim 1, wherein $R^1$ is aminomethylphenyl.

11. A compound according to claim 1, wherein $R^1$ is amidinophenyl.

12. A compound according to claim 1, wherein

Y is 3-$R^2$-azetidino, 2-$R^2$-pyrrolidino, 2-$R^2$-piperidino, 3-$R^2$-piperidino, 4-$R^2$-piperidino, 4-$R^2$-piperazino or 3-$R^2$-4-$R^4$-piperazino;

$R^2$ is —$COOR^3$, —$CH_2COOR^3$ or —$OCH_2COOR^3$; and $R^4$ is —$CH_2COOR^3$.

13. A compound according to claim 1, wherein

Y is 3-($R^3OOC$—$CH_2$—O—)-azetidino, 2-($R^3OOC$—)-pyrrolidino, 2-($R^3OOC$—)-piperidino, 3-($R^3OOC$—)-piperidino, 4-($R^3OOC$—)-piperidino, 4-($R^3OOC$—$CH_2$—)-piperidino, 3-($R^3OOC$—$CH_2$—O—)-piperidino, 4-($R^3OOC$—$CH_2$—O—)-piperidino, 4-($R^3OOC$—$CH_2$)-piperazino or 3-($R^3OOC$—)-4-$R^4$-piperazino;

$R^1$ is 4-cyanophenyl, 4-aminomethylphenyl, 4-amidinophenyl or 4-guanidinomethylphenyl;

$R^3$ is H, $C_1$-$C_4$-alkyl or benzyl; and $R^4$ is H or benzyl.

14. A compound according to claim 1, wherein

Y is 4-($R^3OOC$—)-piperidino or 4-($R^3OOC$—$CH_2O$—)-piperidino;

$R^1$ is 4-cyanophenyl, 4-aminomethylphenyl or 4-amidinophenyl; and $R^3$ is H, $C_1$-$C_4$-alkyl or benzyl.

15. A compound according to claim 1, wherein said compound is: 1-(3-(4-amidinophenyl)-2-oxo-5-oxazolidinylmethyl)piperidine-4-carboxylic acid or salt thereof.

16. A pharmaceutical composition comprising an effective amount of a compound according to claim 1 and a physiologically acceptable carrier.

17. A composition according to claim 15, wherein said composition contains 5 mg–1 g of said compound.

18. A method of inhibiting the binding of fibrinogen, fibrinectin or von Willebrand factor to a fibrinogen receptor comprising administering a compound according to claim 1.

19. A method of claim 17, wherein the binding inhibition inhibits thrombocyte aggregation.

20. A method according to claim 17, wherein aid compound is administered in a daily dosage of 0.1–20 mg/kg of body weight.

21. A method of claim 17, wherein the binding inhibition provides treatment of thrombosis, apoplexy, cardiac infarctus, inflammation or arteriosclerosis.

22. A method of claim 17, wherein the binding inhibition inhibits the formation of microthrombi between fibrinogen and tumor cells.

\* \* \* \* \*